United States Patent
Tiirola

(10) Patent No.: US 9,869,672 B2
(45) Date of Patent: Jan. 16, 2018

(54) METHOD FOR MEASURING CHEMILUMINESCENCE

(71) Applicants: Ilari Maasilta, Jyväskylä (FI); Marja Tiirola, Kuivasmäki (FI)

(72) Inventor: Marja Tiirola, Kuivasmäki (FI)

(73) Assignee: JYVÄSKYLÄN YLIOPISTO, Jyväskylän Yliopisto (FI)

( * ) Notice: Subject to any disclaimer, the term of this patent is extended or adjusted under 35 U.S.C. 154(b) by 86 days.

(21) Appl. No.: 14/382,512

(22) PCT Filed: Mar. 19, 2013

(86) PCT No.: PCT/FI2013/050308
§ 371 (c)(1),
(2) Date: Sep. 2, 2014

(87) PCT Pub. No.: WO2013/140040
PCT Pub. Date: Sep. 26, 2013

(65) Prior Publication Data
US 2015/0065370 A1    Mar. 5, 2015

Related U.S. Application Data

(60) Provisional application No. 61/612,476, filed on Mar. 19, 2012.

(30) Foreign Application Priority Data

Mar. 19, 2012 (FI) .................................. 20125303

(51) Int. Cl.
C12Q 1/68 (2006.01)
G01N 33/543 (2006.01)
(Continued)

(52) U.S. Cl.
CPC ... *G01N 33/54373* (2013.01); *G01N 27/4145* (2013.01); *G01N 33/60* (2013.01); *G03C 5/26* (2013.01)

(58) Field of Classification Search
None
See application file for complete search history.

(56) References Cited

U.S. PATENT DOCUMENTS 4,035,155 A      7/1977  Durie et al.
4,968,400 A *  11/1990  Shimomura ........... C12Q 1/004
                                                                  204/403.11

(Continued)

FOREIGN PATENT DOCUMENTS

| EP | 0916998 A1 | 5/1999 |
|---|---|---|
| JP | 2009-162519 A | 7/2009 |
| WO | WO 2010/142773 A2 | 12/2010 |

OTHER PUBLICATIONS

European Search Report issued in European Patent Application No. 13764018.1 dated Nov. 3, 2015.
(Continued)

*Primary Examiner* — Betty J Forman
(74) *Attorney, Agent, or Firm* — Birch, Stewart, Kolasch & Birch, LLP

(57) ABSTRACT

The present invention provides a method for determining radioactivity in an ion-sensitive field effect transistor array, the method comprising the steps of incubating the array with electron-sensitive silver-halide material and then incubating the array with a developer solution reducing the silver halides that have been exposed to radioactivity to elemental silver and simultaneously measuring pH at each separate reaction chambers, wherein decrease of the pH indicates the presence of radioactivity in a reaction chamber.

6 Claims, 3 Drawing Sheets

Figure 1:
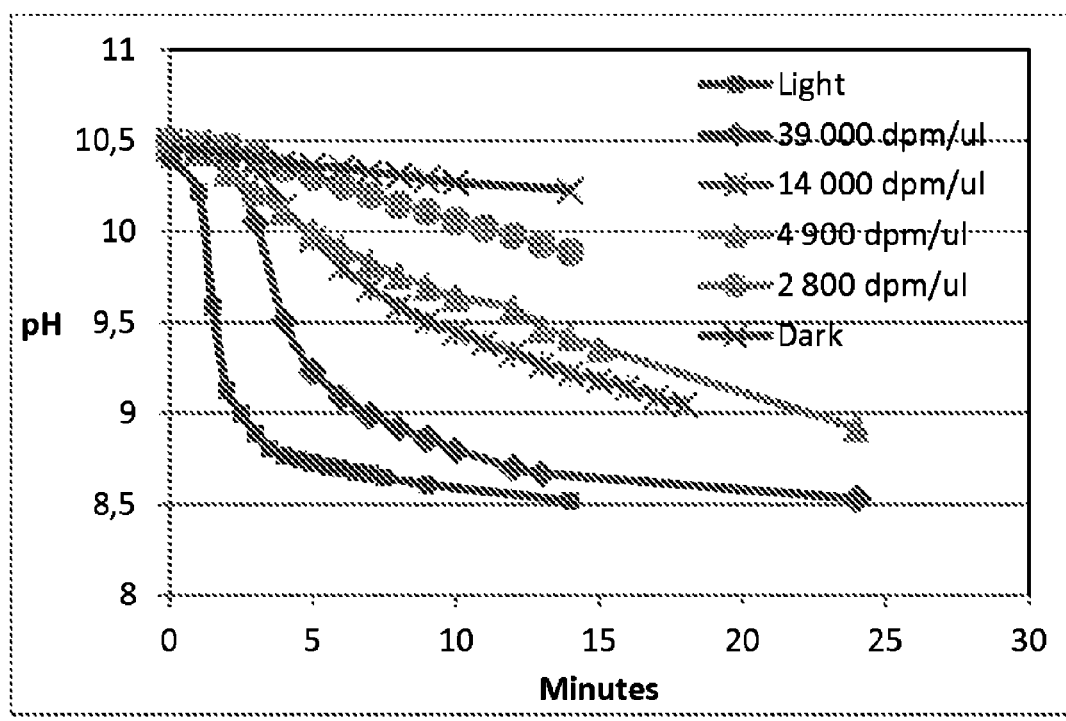

(51) Int. Cl.
*G01N 27/414* (2006.01)
*G01N 33/60* (2006.01)
*G03C 5/26* (2006.01)

(56) References Cited

U.S. PATENT DOCUMENTS

| | | | |
|---|---|---|---|
| 5,236,816 | A | 8/1993 | Purol et al. |
| 2002/0142411 | A1 | 10/2002 | Hainfeld |
| 2005/0123440 | A1* | 6/2005 | Wien ........................ C12Q 1/10 |
| | | | 422/400 |
| 2006/0115857 | A1 | 6/2006 | Keen |
| 2008/0145869 | A1* | 6/2008 | Ohzeki ................ G01N 33/582 |
| | | | 435/7.9 |
| 2009/0014757 | A1 | 1/2009 | Takulapalli et al. |
| 2009/0026082 | A1 | 1/2009 | Rothberg et al. |
| 2010/0059391 | A1* | 3/2010 | Ying .................. G01N 33/5438 |
| | | | 205/792 |
| 2011/0014633 | A1* | 1/2011 | Ifuku ................ G01N 33/5438 |
| | | | 435/7.9 |
| 2012/0034607 | A1 | 2/2012 | Rothberg et al. |

OTHER PUBLICATIONS

International Search Report, issued in PCT/FI2013/050308, dated Jul. 15, 2013.
Search Report issued in Finland priority application 20125303, dated Jan. 25, 2013.
Written Opinion of the International Searching Authority, issued in PCT/FI2013/050308, dated Jul. 15, 2013.

\* cited by examiner

METHOD FOR MEASURING CHEMILUMINESCENCE

CROSS REFERENCE TO RELATED APPLICATIONS

This application is the National Phase of PCT/FI2013/050308 filed on Mar. 19, 2013, which claims priority under 35 U.S.C. 119(e) to U.S. Provisional Application No. 61/612,476 filed on Mar. 19, 2012, and under 35 U.S.C. 119(a) to Patent Application No. 20125303 filed in Finland on Mar. 19, 2012, all of which are hereby expressly incorporated by reference into the present application.

FIELD OF THE INVENTION

The present invention relates to a method for measuring radioactivity of biomolecules using semiconductor pH sensors, which allow analysis in small volumes and array format. Particularly, the invention provides a method for determining radioactivity of nucleic acids or nucleic acid binding molecules using non-optical massive-parallel sequencing assays. The invention also provides a method for determining the concentration of multiple proteins or antibodies in samples using antibody sandwich technology when analysing with semiconductor sensors.

BACKGROUND OF THE INVENTION

Parallel analysis of thousands of biomolecules, like nucleic acids and proteins, and their specific properties is a challenge in biochemistry, genetics, medical diagnostics and microbiology.

Microarrays have proven useful in providing targeted DNA sequence information of the presence and concentration of many thousands of specific genetic regions in a single test. They can be used e.g. to identify novel genes, binding sites of transcription factors, changes in gene copy numbers, complex mutations in disease-causing human genes as well as to study microbial diversity in the environment. Microarrays also serve as a demultiplexing tool to sort spatially the sequence-tagged products of parallel reactions performed in solution (Stoughton et al., 2005). Microarrays can be printed from a set of pre-synthesized single-stranded DNA probes (oligonucleotides) or constructed using on-plate synthesis of the designed probes (Šášik et al., 2004). In the technology patented by Illumina (Chee et al., 2006, 2007) microarrays comprise of thousands of microwells, each containing a single bead carrying $10^5$ homologous probes. Beads are originally scattered randomly across the microarray and then decoded by sequential probing system, so that in the end each chip has a unique address file which encodes the identity of each bead. All these microarrays are analyzed using CCD-cameras or laser technology to detect fluorescence or chemiluminescence signals. Regardless of the current microarray technology, the raw data always comes in the scanned image, thus needing expensive high-resolution detectors and specific software for image analysis.

DNA sequencing technology has allowed analysis of millions of sequences in parallel (massively-parallel sequencing, also known as high-throughput sequencing or next-generation sequencing NGS) (e.g. Margulies et al., 2005, Rothberg & Leamon, 2008, Rothberg et al., 2011). Development of the new sequencing technology has largely replaced the need of prearranged microarrays. Still neither of the methods, high-throughput sequencing and microarray hybridization analysis, can alone offer a direct solution for the simultaneous analysis of the identity and labelling of a set of unknown nucleic acids. To study DNA-protein interactions, like histone modifications or transcription factor binding sites, chromatin immunoprecipitation (ChIP) can be used to separate targets of interest, based on the antibody precipitation and analysis of this way separated DNA using sequencing (ChIP-seq) or microarray technology (ChIP-chip) (reviewed by Hoffman & Jones, 2009). Another method for separating the functionally interesting nucleic acid from the sample is DNA stable isotope probing (DNA-SIP) by isolating heavier $^{13}$C-labelled DNA from the lighter unlabelled $^{12}$C-DNA by density-gradient ultracentrifugation (Radajewski et al., 2000, 2003). A recent microarray technique named as CHIP-SIP (Pett-Ridge et al., 2010, 2011; Mayali et al., 2011) has been introduced to analyse stable isotope labelled RNA hybridized on the pre-designed oligonucleotides on the microarray, with the detection using Nano-SIMS (nanoscale resolution secondary ionization mass spectrometer). Spatial distribution of radioactive objectives (like labelled biomolecules or microbes in tissue samples) can be determined by linking the microautoradiography image with in situ hybridization image in the protocol of MAR-FISH, microautoradiography-fluorescence in situ hybridization (Lee et al., 1999), which is done using fluorescence microscope imaging. "Isotope arrays" have been designed to study certain groups of substrate-consuming microorganisms by selecting their nucleic acids in a phylogenetic microarray by hybridization to phylogenetically designed oligonucleotides and determining the radioactivity of these microarray spots using autoradiographic x-ray film (Adamczyk et al., 2003, Wagner et al., 2006). In target enrichment platforms (like Agilent Sure select platform) nucleic acids with certain sequence motifs are separated by hybridization, then followed by sequencing of the separated nucleic acids. Target enrichment is useful for focusing the NGS workflow on key genomic regions of interest, while reducing cost per sample. Selecting target regions of interest e.g. only exon regions or expressed kinases enable thus more powerful and cost-efficient studies of genetic diversity.

Currently there are several manufacturers offering instruments for high-throughput sequencing (e.g. trademarks Illumina, 454/Roche, PacBio and Ion Torrent) of which Ion Torrent utilizes semiconductor technology and uses ion-sensitive, field-effect transistor (ISFET) arrays (Bergveld, 2003). Use of this technology, compatible with complementary metal-oxide semiconductor (CMOS) processes (Yeow et al., 1997) have enabled construction of miniaturized circuits in tiny microchips and constructing integrated circuits for low-cost sequencing devices (Rothberg et al., 2011). Sequencing using ISFETs is based on the measurement of the hydrogen ion concentration of a solution (commonly denoted as "pH") (Rothberg & Hinz, 2009). In this technology sequence data are obtained by directly sensing the ions (pH) produced by template-directed DNA polymerase synthesis without light signal and image analysis. However, the semiconductor microchip has not been used for downstream analyses, like the analysis of radioactivity or chemiluminescence, as there has not been methods for the analysis of those parameters through the pH change.

Since the $18^{th}$ century it has been known in photography that silver halides (like AgBr, AgI and AgCl) are light-sensitive forming metallic silver when exposed to light (Rieke, 2003). The silver-halide in light-sensitive photographic material is in small grains of size ~1 μm, and photons of high enough energy can create a free photoelectrons, which can then reduce the silver ions into small atomic silver clusters, forming a "latent" image in these grains.

When the photographic material is then developed by a strongly reducing chemical agent, the reduced (latent) metallic silver cluster (even 3-4 Ag atoms) can catalyze the reduction of the entire grain, leading to a large number of $10^{10}$ to $10^{11}$ reduced metallic Ag atoms in a grain, and a tremendous intensification of the latent image. The photographic contrast arises, because during film development the reducing agent, typically hydroquinone, selectivity reduces only those grains, which contain atomic silver clusters, if the development process is performed under correct conditions (time, temperature and developer concentration). The developing agent in the developer solution is ionized, and these ions supply electrons to the silver ions of the exposed silver halide grains, reducing them to solid silver. Hydroquinone can also be replaced by ascorbic acid, or vitamin C, which, however, suffers from poor stability. This is because oxidation by-products formed during the development are acidic, retarding the development in and adjacent to areas of high activity. This also explains why ascorbate developers have poor keeping properties, as oxidised ascorbate is both ineffective as a developing agent and lowers the pH of the solution, making the remaining developing agents less active. Practical methods to improve the stability of ascorbate developer have been sought.

In autoradiography, instead of light, radioactivity is used for the direct sensitization of the light- and high-energy particle-sensitive material. An autoradiograph is an image on an x-ray film or on a nuclear emulsion (a photographic emulsion optimized for particle detection), produced by the pattern of decay emissions (e.g. alpha- or beta particles or gamma rays) from a distribution of a radioactive substance. Alternatively, the autoradiograph is also available as a digital image (digital autoradiography), due to the development of scintillation gas detectors (Barthe et al., 1999) or rare earth phosphorimaging systems (photostimulable phosphor plate).

When the autoradiography of radioactive material happens using x-ray film or nuclear emulsion for radiolabelled proteins, nucleic acids or entire organisms, a latent image is first formed just like in the exposure by light. However, when β-emitters (e.g. $^{14}C$, $^{3}H$, $^{35}S$, $^{32}P$, $^{33}P$) are used, the original high-energy electron and the secondary electrons it produces directly cause the reduction of the Ag ions to metallic silver (Erskine, 1979).

Autoradiography provides an alternative to direct radiation detection by solid state detectors such as Si p-n junctions, Li-drifted Si detectors or scintillation detectors (Knoll, 2010). The advantages of autoradiography over solid state detectors are: simplicity, reliability, stability, low cost, large dynamic range, and especially the fact that there is no count rate limitation, contrary to all types of solid-state detectors. It cannot, however, measure the emitted energy spectrum or work in real-time but in the present invention neither of these is required.

The present invention is directed to a problem how to detect radioactivity of multiple biomolecules in an array format. The solution provided by the invention is a method wherein the ion-sensitive field effect transistor array is incubated in a microautoradiographic emulsion so that radioactivity forms a latent image, which exponentially accelerates silver halide reduction to metallic silver when the emulsion is developed. This reduction will cause a pH decrease in unbuffered developer solutions (i.e. a developer with low buffer capacity), which can be measured using pH sensors provided by said array, thus providing information of thousands of separate biomolecules at the same time.

SUMMARY OF THE INVENTION

The object of the present invention is to provide a method for determining radioactivity in an ion-sensitive field effect transistor array, the method comprising the steps of a) attaching molecules of a sample to reaction chambers in said array; b) if said sample does not contain radioactivity, contacting said array with a radioactive molecule specifically binding to a molecule of interest; c) incubating the array with electron-sensitive silver-halide material; and d) incubating the array with a developer solution reducing the silver halides that have been exposed to radioactivity to elemental silver and simultaneously measuring pH at each separate reaction chamber, wherein decrease of the pH indicates the presence of radioactivity in a reaction chamber.

Another object of the present invention is to provide a device comprising an ion-sensitive field effect transistor array, wherein said device is programmed to perform the method as defined in the present invention.

The present invention also provides a kit comprising a first container comprising an electron-sensitive silver-halide material, and a second container comprising a developer solution reducing the silver halides in said electron-sensitive silver-halide material.

A further object of the present invention is to provide a method for determining chemiluminescence in an ion-sensitive field effect transistor array.

A BRIEF DESCRIPTION OF THE DRAWINGS

FIG. 1 shows the pH decrease in Example 1, when Kodak NTB microautoradiographic emulsion was incubated 96 hours with varying amounts of radioactivity (0-39 000 dpm/µl, C-14 labelled substrate initiation) and then measured after starting the development process by adding Instant Mytol developer (pH 11) at time t=0. The pH of the solution was measured using Schott Blue Line 27 pH electrode.

Figure 2:
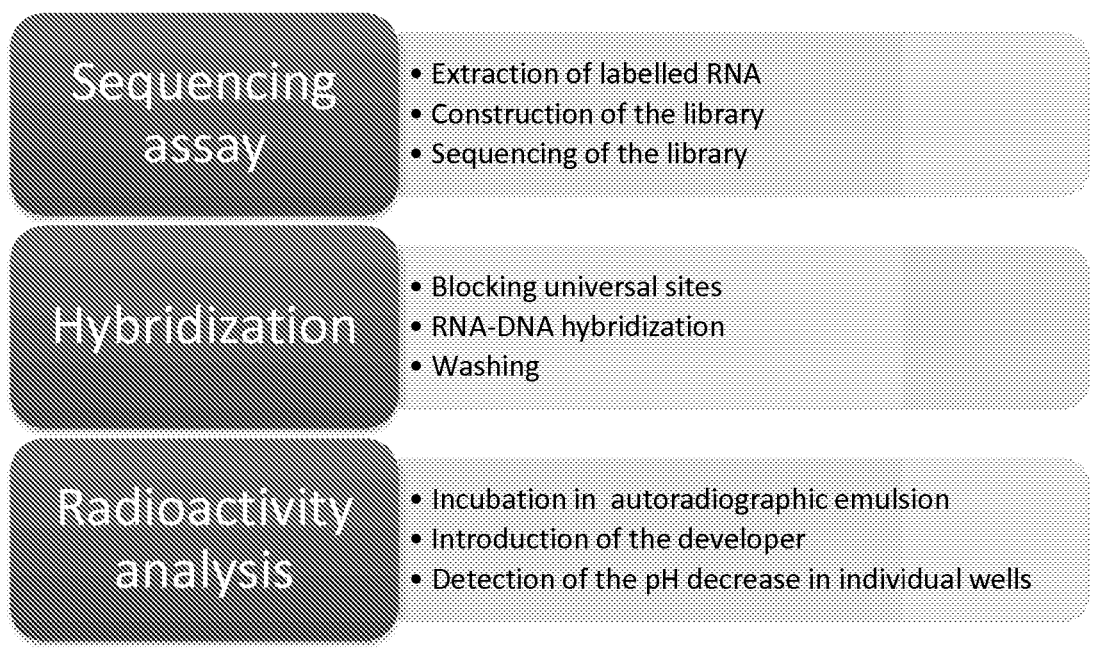

FIG. 2. shows the steps in Example 3, in which the semiconductor array is used for simultaneous sequencing and radioactivity analysis of individual type RNA molecules, like a pool of microbial 16S rRNA after incubation of the environmental sample with $^{14}C$-labelled substrate.

Figure 3:
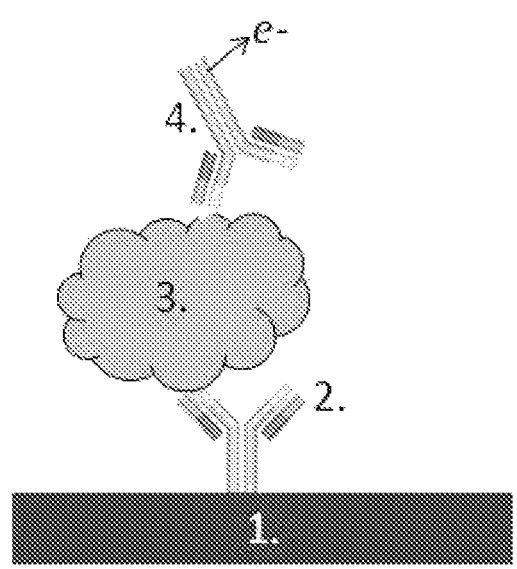

FIG. 3. shows an example of antigen detection by antibody sandwich technology (Example 4). Figure objects: 1. surface for capture antibody attachment and ion sensing layer; 2. capture antibody; 3. protein (antigen); 4. radiolabelled detection antibody emitting electrons in the decay process suitable for measurement through the pH change.

DETAILED DESCRIPTION OF THE PRESENT INVENTION

The invention is based on the observation that the radioactivity of the sample can be analysed using pH change in a microautoradiographic emulsion or film contacted with an ion-sensitive field effect transistor array. The invention is based on the known exponential ($10^{10}$-$10^{11}$ times) increase in the number of metallic silver atoms, if latent metallic silver is available in electron-sensitive microautoradiographic silver-halide emulsion. The invention is based on the observation that when microautoradiographic emulsion is developed in unbuffered (i.e. adding acid to the developer solution decreases the pH), but highly alkaline (e.g. pH 10-11) developer solutions, such as the ascorbic acid developer shown in Exp. 1, radioactivity of the sample can be determined by the decrease in the pH, the speed of which is dependent of the radioactivity and incubation time of the sample. The core of the invention is therefore that the radioactivity of the sample can be measured with a pH measurement, which can be utilized in semiconductor-based assays. The use of this method allows direct measurement of the radioactivity without scanning the image, thereby excluding the need of image analysis. The use of temperature-dependently solidifying microautoradiographic emulsion is beneficial, since solid emulsions states allow washing and addition of developer solutions without diluting or losing the emulsion.

When used together with the semiconductor ISFET technology, the invention provides a method for simultaneous analysis of both the sequence information and radiolabeling of nucleic acids in a way these two features can be linked together. This is possible by first analyzing the sequence information of the molecules and then using the decoded sequences for hybridization of the original sample containing radiolabelled nucleic acids. Using the semiconductor ISFET technology for massively parallel sequencing, sequence data of millions of DNA-molecules are simultaneously sequenced, and the spatial location of the sequence is exactly registered for each sequenced molecule on the microchip.

In a further aspect the invention provides a new method for analyzing protein concentrations using semiconductor technology. In this application radiolabeled molecules can be detected by their binding to their specific antibodies on semiconductor-based assays. The same methodology can also be used for analyzing antibody concentrations.

The term "silver halide" refers to silver bromide (AgBr), chloride (AgCl), iodide (AgI), and to three forms of silver fluorides. Although most silver halides involve silver atoms with oxidation states of +1 ($Ag^+$), silver halides in which the silver atoms have oxidation states of +2 ($Ag^{2+}$) are known, of which silver(II) fluoride is the only one known to be stable.

Accordingly, the present invention is directed to a method for determining radioactivity in an ion-sensitive field effect transistor array, the method comprising the steps of a) attaching molecules of a sample to reaction chambers, such as microwells, in said array; b) if said sample does not contain radioactivity, contacting said array with a radioactive molecule or radioactive molecules with specific binding properties so that said radioactive molecule or radioactive molecules bind(s) to the specific target molecule(s) of the sample, if said target molecule(s) is/are present in the sample; c) incubating the array with electron-sensitive silver-halide material; and d) incubating the array with a developer solution reducing the silver halides that have been exposed to radioactivity to elemental silver and simultaneously measuring pH at each separate reaction chamber, wherein decrease of the pH indicates the presence of radioactivity in a reaction chamber.

In embodiments of the invention, said sample preferably comprises nucleic acid molecules, e.g., said sample can contain DNA prepared for sequencing. The present method is thus also directed to sequencing of the nucleic acid molecules attached to the array so that the sequencing is performed before the array is contacted with said radioactive molecule, which preferably is a radioactively labelled nucleic acid, or nucleic acid specific binding protein or antibody. However, the method of invention can also be performed without hybridization step b), if the radioactivity is already present in the bound molecules to be sequenced. In the sequencing methods of the present invention particularly, the nucleic acid molecules to be sequenced can be attached to a reaction chamber in said array through a support material such as a microbead.

In another embodiment of the invention, said sample comprises peptides or polypeptides, which are attached to the array in step a). Preferably, the reaction chambers of the array are coated with antibodies before attaching the peptide or polypeptides of the sample to said array. Generally, said radioactive molecule in step b) is a radioactively labelled antibody.

In another aspect of the invention, the radioactive signal can be replaced by chemiluminescence signal (see Example 2), in which emission of electromagnetic radiation is formed during the course of chemical reactions. Chemiluminescence can also cause latent image in the microautoradiographic emulsion, when an enzymatic molecule, e.g., peroxidase enzyme, such as horseradish peroxidase, or alkaline phosphatase and a substrate are contacted with each other, or, e.g., luciferin is oxidized by luciferase. For example, a light emitting reaction occurs when luminol and hydrogen peroxide are mixed in the presence of a suitable catalyst (iron or copper, or an auxiliary oxidant). Other suitable chemiluminescent substrates are dioxetane, acridinium ester, hydrazide and luciferin. The chemiluminescence causing enzymatic molecule or enzymatic molecules are conjugated to molecules (antibodies, proteins, single stranded nucleic acids), which have specific binding properties to the samples in an array through protein-antibody recognition or nucleic acid hybridization. The conjugation of the recognition molecule and the chemiluminescence forming partner can be performed using protein fusion, avidin-biotin conjugation or other available conjugation systems, which can be used for conjugating molecules (proteins and/or nucleic acids) together.

Accordingly, the present invention is also directed to a method for determining chemiluminescence in an ion-sensitive field effect transistor array, the method comprising the steps of a) attaching molecules of a sample to reaction chambers, e.g., microwells, in said array; b) contacting said array with an chemiluminescence causing enzymatic molecule or enzymatic molecules that are conjugated to molecules with specific binding properties so that the conjugate(s) bind(s) to the specific target molecule(s) of the sample, if said target molecule(s) is/are present in the sample; c) incubating the array with electron-sensitive silver-halide material and a chemiluminescence substrate; and d) incubating the array with a developer solution reducing the silver halides that have been exposed to chemiluminescence light to elemental silver and simultaneously measuring pH at each separate reaction chamber, wherein decrease of the pH indicates the presence of chemiluminescence in a reaction chamber.

In a further aspect, the invention provides methods of making diagnostic antibody microarrays using the same semiconductor technology. In the proposed arrays, binding antibodies are spotted or otherwise attached and decoded on the surface of the semiconductor sensors and radiolabelled secondary antibodies are introduced together with the samples. Radioactivity can be measured as in sequencing arrays by incubation with silver-halide emulsion, introduction of the developer and measurement using the pH sensor.

The present invention is further directed to a device comprising an ion-sensitive field effect transistor array, wherein said device is programmed to perform the method according to the present invention. The device also comprises control circuitry coupled to the array and configured to generate at least one array output signal to provide multiple frames of data from the array at a frame rate of at least 1 frame per second. In one aspect, the frame rate may be at least 10 frames per second. In another aspect, the frame rate may be at least 20 frames per second. In yet other aspects, the frame rate may be at least 30, 40, 50, 70 or up to 100 frames per second. One embodiment of the invention is a use of said device for performing the method for detecting radioactivity or chemiluminescence as described above.

The present invention is also directed to a kit for performing the method of the present invention comprising an electron-sensitive silver-halide material, and a developer solution reducing the silver halides in said electron-sensitive silver-halide material. Preferably, the kit further comprises an ion-sensitive field effect transistor array. The kit may also comprise reagents for DNA sequencing, a radioactive label, a radioactively labelled nucleic acid, a radioactively labelled antibody, or a chemiluminescent label.

In a preferred embodiment, the developer solution is unbuffered and highly alkaline (e.g. pH 10-11), wherein pH of the developer solution decreases linearly between pH 10 and pH 8 when titrating with an acid. An example of such is the ascorbic acid developer disclosed in Example 1. Buffered solutions consist of mixtures of weak acids and their conjugate bases (or a weak bases and their conjugate acids) resisting changes in pH, but in an unbuffered solution, the introduction of acid or base into the solution drastically alters the pH. Adding just 1 oz. of concentrated (31 percent) hydrochloric acid to a gallon of water, for example, would change the pH of the water from 7 to less than 1. Adding the same amount of acid to a buffered solution, in comparison, would likely lower the pH by only a few tenths of a pH unit. To facilitate the method of this invention it is optimal that the developer solution is unbuffered, showing closely linear decrease in the pH between 10 and 8, when titrating, for instance, with hydrochloric acid. Further, the silver-halide material in the kit should have viscosity suitable for use in the array.

The invention allows economical solutions for DNA, RNA, and protein analysis that can be used for genetic and disease research, drug development, development of molecular tests in the clinic and molecular microbiology. The invention provides secondary use of semiconductor-based sequencing assays as case-by-case microarrays to study concentration and properties of various biomolecules analysed by sequencing.

The publications and other materials used herein to illuminate the background of the invention, and in particular, to provide additional details with respect to its practice, are incorporated herein by reference. The present invention is further described in the following examples, which are not intended to limit the scope of the invention.

EXAMPLES

Example 1. Analysis of Radioactivity Using pH Sensor

The aim of this experiment is to study if the the analysis of radioactivity is possible using ordinary laboratory pH sensor.

An ascorbic-acid based unbuffered developer (Instant Mytol) was made using the following formula (http://www.photosensitive.ca/wp/easy-film-developers):

Start with 750 ml water
60 g sodium sulfite (anhydrous)
11.5 g ascorbic acid
0.15 g 1-phenyl-3-pyrazolidon (Phenidol, pre-dissolved in ethanol)
7 g sodium metaborate
Water to 1 liter.

A 50 ml aliquot of Instant Mytol was adjusted to pH 11 using 1 M NaOH (about 4.8 ml/50 ml Instant Mytol) just before each experiment; 100 µl NaOH addition increased the pH 0.07 unit linearly between 7.84 and 11.00 (y=0.06485x+7.613, $R^2$=0.994). Microautoradiographic emulsion (Kodak NTB, 1 ml) was divided to black microcentrifuge tubes and four different treatments were done in dark room.

A) Exposing the open tube to bright light for 30 seconds, 0 dpm (Light)
B) Adding of 3 900 dpm $^{14}C$ glucose per µl emulsion
C) Adding of 4 900 dpm $^{14}C$ glucose per µl emulsion
D) No treatment (Dark)

The test was repeated with $^{14}C$-leucine:
E) 14 000 dpm per µl emulsion
F) 2 800 dpm per µl emulsion Radioactivity of the emulsions was measured using liquid scintillation counter. After exposing to radioactivity for 96 hours at +4° C., preparation for measurements were done by diluting 100 µl of warmed (37° C.) emulsion with 2 ml of water and adding 100 µl of freshly pH adjusted Instant Mytol developer. Measurements were immediately started with Schott Blue Line 27 pH electrode and continued 14-24 minutes in dark room under red light and continuous stirring.

Results

Light-exposed emulsion (see FIG. 1 "Light") developed quickly, which led to a dramatic decrease of the pH of the mixture. Samples incubated with radioactive substrates also caused pH decrease in the emulsion/developer solution, and the rate was dependent on the amount of the radioactivity.

The experiment shows that 2800 dpm/µl is easily differentiated from the background. This means that in a reaction volume of nanoliter, the 2.8 dpm would cause detectable pH change, and in picoliter reaction volume 0.003 dpm would be measurable after 96 hours incubation time. Adjusting silver halide concentration, temperature, time and developer properties the speed and maximum pH change can be further adjusted to allow higher sensitivity.

Example 2. Analysis of Chemiluminescence Using pH Sensor

Analogous to radioactivity, light can accelerate reduction of silver-halide to metallic silver. This experiment demonstrates that chemiluminescence can also be measured using the method, as the speed of pH decrease is relative to the concentration of horseradish peroxidase enzyme in the emulsion solution, when pH of the alkaline developer is not buffered.

Microautoradiographic emulsion (Kodak NTB, warmed to 37° C.) was divided onto 12 wells of a 24-well Elisa plate (Greiner, cat. no. 662150), 0.1 ml for each well, and four different treatments were done in dark room. Streptavidin-POD was provided by Roche Applied Sciences, cat. no. 11089153001. For three extra wells (E) we added 0.1 ml of autoradiographic emulsion, which had been incubated with 14 000 dpm/µl of $^{14}C$-leucine for 1488 hours (see Example 1). Triplicate treatments were as follows:

A) No additions (control)
B) Adding of 0.01 mU Streptavidin-POD per µl emulsion
C) Adding of 0.1 mU Streptavidin-POD per µl emulsion D) Adding of 1 mU Streptavidin-POD per μl emulsion
E) Emulsion incubated with 14 000 dpm $^{14}$C-leucine per μl of emulsion for 1488 hours After above additions, 50 μl PS-Atto chemiluminescence reagent (Lumigen Inc.) was added in the tubes (treatments A to D) for 2 min. Then all the emulsions were diluted with 1 ml of water and 200 μl of freshly pH adjusted Instant Mytol developer (pH 11). Measurement of pH was performed using Schott Blue Line 27 pH electrode for 24-27 minutes in dark room under red light.

Results

Radioactivity-exposed emulsion (E) developed most quickly, leading to 2.04 pH unit decrease in 27 min incubation time. The speed of pH decrease was dependent on the amount of the POD enzyme. Some pH decrease was also seen in untreated control sample (A), but the decrease was smaller than in the lowest POD concentration. The speed of the pH decreases (mean±s.d. of triplicates) from the start to the end point of measurement were as follows:
A) 0.0247±0.0012 pH units per minute (Control)
B) 0.0326±0.0016 pH units per minute (0.01 mU POD-conjugate per μl)
C) 0.0372±0.0016 pH units per minute (0.1 mU POD-conjugate per μl)
D) 0.0472±0.0029 pH units per minute (1 mU POD-conjugate per μl)
E) 0.0756±0.0004 pH units per minute (Radioactivity exposed control sample)

Example 3. Analysis of the Radioactivity of a Set of Nucleic Acids

The goal of this experiment is to analyze specific radioactivity for nucleic acids, which in this example are RNA molecules derived from a microbial consortium enriched with radiolabelled substrate ($^{14}CH_4$). The analysis reveals which of the various bacteria have been able to use the substrate and gives a quantitative figure of the radioactivity of each RNA molecule.

Environmental sample is incubated in the in situ conditions with added $^{14}CH_4$. RNA is extracted using standard procedures. A 16S rRNA library is constructed through cDNA synthesis and PCR amplification using universal bacterial 16S rRNA gene specific primers for the *Escherichia coli* region 27 to 338 with additional sequence matching the adapter of the Ion Torrent beads in the reverse primer. The product is further amplified and sequenced using Ion Torrent semiconductor sequencing chemistry towards forward direction until the length of 200 bp.

The Ion Torrent microchip is then hybridized with the original RNA extraction purified using size-selection of the 16S rRNA band. Before that the universal primer site is blocked with an oligonucleotide matching the conservative primer site 338-354 to increase specificity. Hybridization is performed in suitable salt and temperature conditions. After hybridization, unbound RNA sequences are washed.

Microautoradiographic emulsion is melted and introduced to the chamber of the Ion Torrent microchip avoiding any light. Incubation is continued for an hour to one week in darkness, depending on the incorporated radioactivity in the RNA. After incubation, weakly buffered developer solution is injected to the reaction chamber where the emulsion is solidified in the wells of the semiconductor array. The speed of the pH decrease is followed for 20 min to 16 hours, increasing the temperature will speed up the process. The workflow is illustrated in FIG. 2.

Advantages

This experiment shows the workflow how the invention can be practically utilized for extending the use of semiconductor technology from sequencing to microarray type analysis of the radiolabelled RNA molecules. The benefits of this protocol, compared to previous microarray approaches, include: 1) no need of the previous information of the RNA molecules; 2) no need for planning or synthesizing specific probes; 3) exact match of the microarray probes with the sample molecules; 4) quantitative results; and 5) unlimited flexibility to increase/decrease the sensitivity by changing incubation time, developing conditions and developing time.

Example 4. Antigen-Antibody Testing Using Radioactivity and Semiconductor Array

Analysis of radioactivity using semiconductors technology through the change in pH is useful also for diagnostic purposes, especially when the biomolecules are spotted on an array of hundred or more spots that are in certain order. One embodiment of our invention would be an antibody sandwich array of certain viral proteins using radioactively labeled detection antibody.

In this procedure highly specific monoclonal antibodies against different viral capsid antigens are spotted in a known order on 100-1000 grid wells of the pH sensitive semiconductor array. The serum or saliva sample of a patient is prepared and incubated with radioactively labeled anti-viral antibody mixture in the reaction chamber, where the specific monoclonal antibodies capture viral proteins on the surface of grid wells (FIG. 3).

The radioactivity of sandwich complex is determined by addition of the melted autoradiographic emulsion on the assay and incubation 10 min-overnight in total darkness. Incubation is stopped by addition of the developer, as in experiments 1 and 2. The speed of the pH decrease is followed by the semiconductor technology.

Advantages

The major benefits of using radioactivity signal and semiconductor technology in antigen-antibody tests would include: 1) no need for specific laser or CCD camera systems for the analysis of molecules; 2) numeric results are obtained directly from each semiconductor transistor, which can be separated in individual wells; 3) sensitivity can be improved by extended incubation and/or developing times.

REFERENCES

1. Adamczyk, J., Hesselsoe, M., Iversen, N., Horn, M., Lehner, A., Nielsen, P. H., Schloter, M., Roslev, P.& Wagner, M. (2003) The isotope array, a new tool that employs substrate-mediated labeling of rRNA for determination of microbial community structure and function. Appl. Environ. Microbiol. 69(11):6875-87.
2. Barthe, N., Coulon, P., Hennion, C., Ducassou, D., Basse-Cathalinat, B. & Charpak, G. (1999). "Optimization of a new scintillation gas detector used to localize electrons emitted by 99mTc". J. Nucl. Med. 40 (5): 868-75.
3. Bergveld, P. (2003). Thirty years of ISFETOLOGY. What happened in the past 30 years and what may happen in the next 30 years? Sens. Actuators B Chem. 88: 1-20.
4. Chee, M. S., Stuelpnagel, J. R. & Czarnik. A. W. (2006) Method of making and decoding of array sensors with microspheres. U.S. Pat. No. 7,060,431 (Jun. 13, 2006)

5. Chee, M. S., Stuelpnagel, J. R. & Czarnik A. W. (2007) Multiplex decoding of array sensors with microspheres. U.S. Pat. No. 7,226,734 (Jun. 5, 2007).
6. Erskine, J. R. (1979). Nuclear track emulsions. Nucl. Instrum. Methods 162:371-378.
7. Knoll, G. F. (2010). Radiation detection and measurement, 4th Ed. John Wiley& Sons.
8. Lee, N., Jansen, J. C., Aspergren, H., Dircks, K., Henze, M., Schleifer K.-H. & Wagner, M. (2002) Population dynamics and in situ physiology of phoshorus-accumulating bacteria in wastewater treatment plants with enhanced biological phosphorus removal operated with and without nitrogen removal. Water Sci. Technol. 46(1/2):163-170.
9. Lee, N., Nielsen, P. H., Andreasen, K. H., Juretschko S., Nielsen, J. L., Schleifer, K. H. & Wagner, M. (1999) Combination of fluorescent in situ hybridization and micro autoradiography a new tool for structure-function analyses in microbial ecology. Appl. Environ. Microbiol. 65(3):1289-97.
10. Margulies M., Egholm, M., Altman, W. E., Attiya, S., Bader, J. S., Bemben, L. A., Berka, J., Braverman, M. S., Chen, Y. J., Chen, Z., Dewell, S. B., Du, L., Fierro, J. M., Gomes, X. V., Godwin, B. C., He, W., Helgesen, S., Ho, C. H., Irzyk, G. P., Jando, S. C., Alenquer, M. L., Jarvie, T. P., Jirage, K. B., Kim, J. B., Knight, J. R., Lanza, J. R., Leamon, J. H., Lefkowitz, S. M., Lei, M., Li, J., Lohman, K. L., Lu, H., Makhijani, V. B., McDade, K. E., McKenna, M. P., Myers, E. W., Nickerson, E., Nobile, J. R., Plant, R., Puc, B. P., Ronan, M. T., Roth, G. T., Sarkis, G. J., Simons, J. F., Simpson, J. W., Srinivasan, M., Tartaro, K. R., Tomasz, A., Vogt, K. A., Volkmer, G. A., Wang, S. H., Wang, Y., Weiner, M. P., Yu, P., Begley, R. F. & Rothberg, J. M. (2005). Genome sequencing in microfabricated high-density picoliter reactors. Nature 437:376-80.
11. Mayali, X., Weber, P., Brodie, E., Mabery, S., Hoeprich, P. & Pett-Ridge, J. (2011). High-throughput isotopic analysis of RNA microarrays to quantify microbial resource use. ISME J doi:10.1038/ismej.2011.175.
12. Pett-Ridge, J., Hoeprich, P. D., Weber, P.& Brodie, E. K. (2010). Chip-SIP: Quantification of Nucleic Acid Stable Isotope Labeling with Biopolymer Microarrays and Secondary Ionization Mass Spectrometry (SIMS). U.S. Provisional Application No. 61/302,827 (Feb. 9, 2010).
13. Pett-Ridge, J., Hoeprich, P. D., Weber, P. & Brodie, E. K. (2011) Devices, methods and systems for target detection. United States Patent Application 20110195862 (Feb. 8, 2011).
14. Radajewski, S., Ineson, P., Parekh, N. R., & Murrell, J. C. (2000). Stable-isotope probing as a tool in microbial ecology. Nature 403: 646-649.
15. Radajewski, S., McDonald, I. R. & Murrell, J. C. (2003). Stable-isotope probing of nucleic acids: a window to the function of uncultured microorganisms. Curr. Opin. Biotechnol. 14: 296-3023.
16. Rieke G. (2003). Detection of light, $2^{nd}$ Ed. Cambridge Univ. Press
17. Rothberg, J. M. & Hinz, W. (2009) Methods and apparatus for measuring analytes using large scale FET arrays. US patent application 20090026082 (Jan. 29, 2009).
18. Rothberg, J. M., Hinz, W., Rearick, T. M., Schultz, J., Mileski, W., Davey, M., Leamon, J. H., Johnson, K., Milgrew, M. J., Edwards, M., Hoon, J., Simons, J. F., Marran, D., Myers, J. W., Davidson, J. F., Branting, A., Nobile, J. R., Puc, B. P., Light, D., Clark, T. A., Huber, M., Branciforte, J. T., Stoner, I. B., Cawley, S. E., Lyons, M., Fu, Y., Homer, N., Sedova, M., Miao, X., Reed, B., Sabina, J., Feierstein, E., Schorn, M., Alanjary, M., Dimalanta, E., Dressman, D., Kasinskas, R., Sokolsky, T., Fidanza, J. A., Namsaraev, E., McKernan, K. J., Williams, A., Roth, G. T. & Bustillo, J. (2011). An integrated semiconductor device enabling non-optical genome sequencing. Nature 475:348-352.
19. Rothberg, J. M. & Leamon, J. H. (2008) Nature Biotechnology 26(10):1117-1124.
20. Šášik, R., Woelk, C. H. & Corbeil, J. (2004). Microarray truths and consequences. Journal of Molecular Endocrinology 33:1-9.
21. Stoughton, R. B. (2005) Applications of DNA microarrays in biology. Annual Review of Biochemistry 74:53-82
22. Urich, T., Lanzen, A., Qi, J., Huson, D. H., Schleper, C. & Schuster, S. C. (2008). Simultaneous assessment of soil microbial community structure and function through analysis of the meta-transcriptome. PLoS ONE 3(6): e2527.
23. Wagner, M., Nielsen, P. H., Loy, A., Nielsen, J. L. Daims, H. (2006). Linking microbial community structure with function: fluorescence in situ hybridization-microautoradiography and isotope arrays. Current Opinion in Biotechnology 17:83-91.
24. Yeow, T. Haskard, M., Mulcahy, D., Seo, H. & Kwon, D. (1997). A very large integrated pH-ISFET sensor array compatible with standard CMOS processes. Sens Actuators B. Chem. 44:434-440.

The invention claimed is:

1. Method for determining chemiluminescence in an ion-sensitive field effect transistor array comprising the steps of:
   a) attaching molecules of a sample to reaction chambers in said array;
   b) contacting said array with a chemiluminescence causing enzymatic molecule conjugated to a molecule with specific binding properties to said molecules;
   c) incubating the array with light-sensitive silver-halide material and a chemiluminescence substrate to produce chemiluminescence light thereby exposing the light-sensitive silver-halide material to chemiluminescent light;
   d) incubating the array with a developer solution reducing the silver halides that have been exposed to the chemiluminescence light to elemental silver thereby forming or enhancing a latent image; and
   e) determining concentration of the chemiluminescence causing enzymatic molecule by measuring a decrease in pH at each separate reaction chamber, said decrease in pH resulting from latent image formation or latent image enhancement.

2. The method according to claim 1, wherein the chemiluminescence causing enzymatic molecule is selected from the group consisting of horseradish peroxidase, alkaline phosphatase and luciferase.

3. The method according to claim 1, wherein the chemiluminescence substrate is selected from the group consisting of luminol, dioxetane, acridinium ester, hydrazide and luciferin.

4. The method according to claim 1, wherein the developer solution is an unbuffered solution or a solution with a low buffer capacity that has a pH 10-11.

5. The method according to claim 1, wherein the developer solution is an ascorbic acid based unbuffered developer solution.

6. The method according to claim 5, wherein the ascorbic acid based unbuffered developer solution comprises 1-phenyl-3-pyrazolidon.

* * * * *